United States Patent
Amii et al.

(10) Patent No.: US 8,802,886 B2
(45) Date of Patent: Aug. 12, 2014

(54) METHOD FOR PRODUCING AROMATIC DIFLUOROACETIC ACID ESTER

(75) Inventors: Hideki Amii, Kobe (JP); Kenichi Fujikawa, Kobe (JP); Yasutaka Fujioka, Kobe (JP); Makoto Matsuura, Kawagoe (JP)

(73) Assignee: Central Glass Company, Limited, Ube-shi (JP)

( * ) Notice: Subject to any disclaimer, the term of this patent is extended or adjusted under 35 U.S.C. 154(b) by 39 days.

(21) Appl. No.: 13/510,227

(22) PCT Filed: Oct. 26, 2010

(86) PCT No.: PCT/JP2010/068920
§ 371 (c)(1),
(2), (4) Date: May 16, 2012

(87) PCT Pub. No.: WO2011/062033
PCT Pub. Date: May 26, 2011

(65) Prior Publication Data
US 2012/0220795 A1    Aug. 30, 2012

(30) Foreign Application Priority Data

Nov. 18, 2009   (JP) .................................. 2009-263316

(51) Int. Cl.
*C07C 69/74*   (2006.01)

(52) U.S. Cl.
USPC .................................... 560/1; 560/8; 560/129

(58) Field of Classification Search
None
See application file for complete search history.

(56) References Cited

FOREIGN PATENT DOCUMENTS

| EP | 1 916 239 A1 | 4/2008 |
| JP | 2000-229987 A | 8/2000 |
| JP | 2002-47293 A | 2/2002 |

OTHER PUBLICATIONS

Uneyama et al. Chem. Commun. (1999), pp. 613-614.*
Amii et al., "A Practical and Highly Efficient Synthesis of α-(Trimethylsilyl)-difluoroacetates", Synthesis, No. 14, 2000, pp. 2001-2003.
Fujikawa et al., "Keiso Kagobutsu no Cross Cupling Hanno ni yoru 2-Aryldifluoro Sakusan Ester no Gosei", 90th Annual Meeting of Chemical Society of Japan in Spring Koen Yokoshu IV, 2010, p. 1344.
International Search Report for PCT/JP2010/068920 dated Dec. 14, 2010.
Sato et al., "Reactions of ethyl bromodifluoroacetate in the presence of copper powder", Journal of Fluorine Chemistry, 125, 2004, pp. 509-515.
Sato et al., "Synthesis of Alkenyl- and Aryldifluoroacetate Using a Copper Complex from Ethyl Bromodifluoroacetate 1)", Chem. Pharm. Bull., vol. 47, No. 7, 1999, pp. 1013-1016.
Uneyama et al., "Defluorinative silylation toward a selective preparation of α-trimethylsilyl-α, α-difluoroacetates from trifluoroacetates", Chem. Communications, 1999, pp. 613-614.
Uneyama et al., "Electroreductive Defluorination of Trifluoromethyl Ketones and Trifluoroacetic Acid Derivatives", J. Org. Chem., vol. 64, No. 18, 1999, pp. 6717-6723.
Extended European Search Report issued Apr. 8, 2014, in European Patent Application No. 10831429.5.
Taguchi et al., "Synthesis of 2,2-difluoroesters by Iododifluoroacelate-Copper with Organic Halides," Tetrahedron Letters (1986), vol. 27, No. 50, pp. 6103-6106.

* cited by examiner

*Primary Examiner* — Patrick Lewis
(74) *Attorney, Agent, or Firm* — Birch, Stewart, Kolasch & Birch, LLP

(57) ABSTRACT

Disclosed is a method for producing a compound having a difluoromethylene group at an even lower cost and with excellent yield. The production method of the present invention is a method for producing an aromatic difluoroacetic acid ester, which comprises reacting an iodobenzene containing an electro attracting group and an α-silyl difluoroacetic acid ester in the presence of a metal halide.

9 Claims, No Drawings

METHOD FOR PRODUCING AROMATIC DIFLUOROACETIC ACID ESTER

TECHNICAL FIELD

The present invention relates to a method for producing an aromatic compound having a difluoroacetic acid ester group.

BACKGROUND ART

Recently, attention has been given to methods for synthesizing a compound having a difluoromethylene group because the compound has a specific biological activity. The method in which a carbonyl group, a thiocarbonyl group or a thioacetal group is reacted with DAST (dimethyl amino sulfide trifluoride) for conversion into a difluoromethylene group (DAST method) and methods in which a halodifluoromethyl group is dehalogenated to provide a difluoromethylene group (e.g., Kumadaki method) are well known (Non-patent document 1).

However, the DAST method is provided at a high cost and has problems such as use of a reaction agent and a substrate which cannot be easily obtained or handled. The Kumadaki method also has problems such as high cost because of the necessity of 2 equivalents of copper atom as a catalyst for completion of reaction.

PRIOR ART DOCUMENTS

Non-Patent Documents

Non-patent document 1: K. Sato et al., Chem. Pharm. Bull., vol. 47, p. 1013 (1999)

SUMMARY OF THE INVENTION

Problems to be Solved by the Invention

Under the above-described circumstances, it has been desired to develop a method for producing a compound having a difluoromethylene group at an even lower cost and with excellent yield.

Means for Solving the Problems

The present invention was made in consideration of the above-described circumstances, and provides a production method, etc. described below, i.e., a method for producing an aromatic difluoroacetic acid ester, which comprises reacting an iodobenzene having an electroattracting group (polar functional group) and an α-silyl difluoroacetic acid ester in the presence of a metal halide, etc.

(i) A Method for Producing a Compound Represented by the Following General Formula (3):

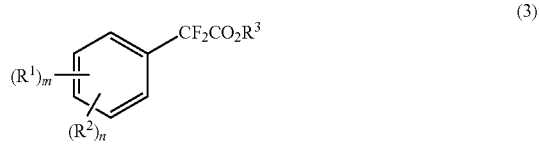

wherein in the general formula (3), $R^1$ each independently represents an electroattracting group, $R^2$ each independently represents a monovalent organic group, $R^3$ represents a monovalent organic group, m is an integer from 1 to 3 and n is an integer from 0 to (5-m), the compound being obtained by reacting a compound represented by the following general formula (1):

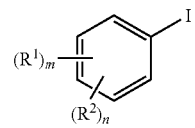

wherein in the general formula (1), $R^1$ each independently represents an electroattracting group, $R^2$ each independently represents a monovalent organic group, m is an integer from 1 to 3 and n is an integer from 0 to (5-m), and a compound represented by the following general formula (2):

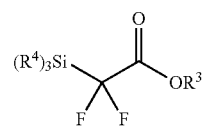

wherein in the general formula (2), $R^3$ represents a monovalent organic group and $R^4$ each independently represents at least one selected from the group consisting of a substituted or unsubstituted methyl group, ethyl group, propyl group, isopropyl group and phenyl group, in the presence of a metal halide.

Examples of the metal halide in the production method of (i) above include potassium fluoride or copper iodide.

(ii) A Method for Producing a Compound Represented by the Following General Formula (4):

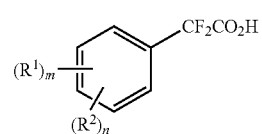

wherein in the general formula (4), $R^1$ each independently represents an electroattracting group, $R^2$ each independently represents a monovalent organic group, m is an integer from 1 to 3 and n is an integer from 0 to (5-m), the compound being obtained by hydrolyzing the compound obtained by the production method of (i) above.

Examples of $R^1$ in the production methods of (i) and (ii) above include a linking group in the ortho position and/or the meta position, and specific examples thereof include at least one selected from the group consisting of a cyano group, a nitro group, a substituted or unsubstituted alkylacetic acid ester group, a substituted or unsubstituted alkylcarbonyl group, a halogen group and a substituted or unsubstituted phenyl group.

Examples of $R^2$ include at least one selected from the group consisting of an alkyl group, a cycloalkyl group, an aryl group, an alkenyl group and an alkynyl group.

Examples of $R^3$ include at least one selected from the group consisting of an alkyl group, a cycloalkyl group, an aryl group, an alkenyl group and an alkynyl group.

Examples of the compound represented by the general formula (2) in the production method of (i) above include a compound obtained by reacting a compound represented by the following general formula (5):

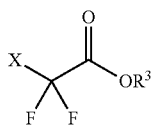

(5)

wherein in the general formula (5), R³ represents a monovalent organic group and X represents a halogen group (e.g., a chlorine atom), and a compound represented by the following general formula (6):

$(R^4)_3SiX$ (6)

wherein in the general formula (6), R⁴ each independently represents at least one selected from the group consisting of a substituted or unsubstituted methyl group, ethyl group, propyl group, isopropyl group and phenyl group, and X represents a halogen group (e.g., a chlorine atom). In this regard, examples of the reaction include a reaction performed in the presence of magnesium.

Effect of the Invention

According to the present invention, it is possible to provide a method for producing a compound having a difluoromethylene group at an even lower cost and with excellent yield. When using the method of the present invention, for example, it is possible to produce an aromatic difluoroacetic acid ester or aromatic difluoroacetic acid at a low cost and with a high yield.

BEST MODE FOR CARRYING OUT THE INVENTION

Hereinafter, the present invention will be described in detail. The scope of the present invention is not limited to the description. In addition to the following examples, the present invention can be suitably changed and then practiced within a range in which the effects of the present invention are not reduced. Note that the entire specification of Japanese Patent Application No. 2009-263316 (filed on Nov. 18, 2009), to which priority is claimed by the present application, is incorporated herein. In addition, all the publications such as prior art documents, laid-open publications, patents and other patent documents cited herein are incorporated herein by reference.

As described above, the method for producing an aromatic difluoroacetic acid ester of the present invention (hereinafter sometimes referred to as the production method of the present invention) is a method for producing a compound represented by general formula (3) (i.e., an aromatic difluoroacetic acid ester) by reacting a compound represented by general formula (1) and a compound represented by general formula (2) in the presence of a metal halide.

In this regard, in the compound represented by general formula (1):

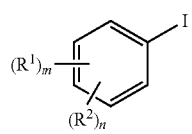

(1)

R¹ each independently represents an electroattracting group. Preferred examples of the electroattracting group include, but are not limited to, —CN, —NO₂, —C(O)OC₂H₅, COCH₃, —Br and -Ph (phenyl group), and among them, —CN and —C(O)OC₂H₅ are more preferred.

Further, R¹ is preferably a group binding to a carbon atom in the ortho position and/or the para position of an iodobenzene ring, but is not limited thereto. The number of R¹(s) binding to the iodobenzene ring (m) is an integer from 1 to 3, and preferably 1. Specifically, examples of preferred embodiments thereof include those in which —CN, —NO₂, —C(O)OC₂H₅, —COCH₃, —Br or -Ph binds to the para position of the iodobenzene ring and an embodiment in which —NO₂ binds to the ortho position of the iodobenzene ring.

In general formula (1), R² each independently represents a monovalent organic group. Preferred examples of the monovalent organic group include, but are not limited to, an alkyl group, a cycloalkyl group, an aryl group, an alkenyl group and an alkynyl group, and among them, an alkyl group is more preferred. The alkyl group as R² is preferably a linear or branched alkyl group having 1 to 16 carbon atoms, but is not limited thereto. Any carbon atom of the alkyl group may be substituted with any number and any combination of a halogen atom, an alkoxy group, a haloalkoxy group, an alkylamino group, an alkylthio group, a cyano group, an aminocarbonyl group (CONH₂), an aryl group, etc. The number of R²(s) binding to the iodobenzene ring (n) is an integer from 0 to (5-m), and preferably an integer from 0 to 2. When R² binds to the iodobenzene ring, R² preferably binds to the meta position, but there is no limitation on the matter.

In the compound represented by general formula (2):

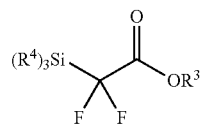

(2)

R³ represents a monovalent organic group. Preferred examples of the monovalent organic group include, but are not limited to, an alkyl group, a cycloalkyl group, an aryl group, an alkenyl group and an alkynyl group, and among them, an alkyl group is more preferred, and an ethyl group is particularly preferred. The alkyl group as R³ is preferably a linear or branched alkyl group having 1 to 16 carbon atoms, but is not limited thereto. Any carbon atom of the alkyl group may be substituted with any number and any combination of a halogen atom, an alkoxy group, a haloalkoxy group, an alkylamino group, an alkylthio group, a cyano group, an aminocarbonyl group (CONH₂), an aryl group, etc.

In general formula (2), it is preferred that R⁴ each independently is a substituted or unsubstituted methyl group, ethyl group, propyl group, isopropyl group, phenyl group or the like, and among them, a methyl group and an ethyl group are more preferred, and a methyl group is particularly preferred. There is no limitation on the embodiment of the substitution, and any number and any combination may be employed in the substitution.

The compound represented by general formula (2) can be obtained, for example, by reacting a compound represented by general formula (5) and a compound represented by general formula (6).

In the compound represented by general formula (5):

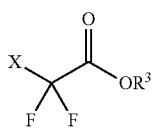

(5)

$R^3$ represents a monovalent organic group, and specifically, the explanation regarding the general formula (2) above can be similarly applied thereto. In general formula (5), X represents a halogen group. Preferred Examples thereof include Cl, Br and I, and Cl (chlorine atom) is more preferred.

In the compound represented by general formula (6):

$(R^4)_3SiX$ (6)

specifically, the explanation regarding the general formulae (2) and (5) above can be similarly applied to $R^4$ and X.

Regarding the reaction between the compound represented by general formula (5) and the compound represented by general formula (6), for example, the compounds may be mixed together under an inert gas atmosphere such as nitrogen and argon in a solvent that is inactive under the reaction condition, and there is no limitation on the matter. Preferred examples of the solvent include those described later as solvents that can be used in the production method of the present invention. Further, in the reaction, the reaction temperature is preferably 20 to 50° C., the mixing time (stirring time) is preferably 1 to 2 hours, and the reaction pressure may be around ordinary pressure. Moreover, the reaction is preferably performed in the presence of magnesium because the reaction can be promoted thereby, but is not limited thereto. Methods of extraction, purification, etc. of the produced compound (the compound represented by general formula (2)) from the reaction system are not particularly limited, and conventionally known methods of extraction, purification, etc. can be suitably employed.

Preferred examples of the metal halide used for the reaction between the compound represented by general formula (1) and the compound represented by general formula (2) in the production method of the present invention include, but are not limited to, potassium fluoride (KF) and copper iodide (CuI). In particular, potassium fluoride is more preferred because it can further increase the yield of the reaction product. The amount of the metal halide to be used is not limited, but for example, the metal halide is preferably used in an amount of 0.2 to 4 equivalents, and more preferably 0.2 to 1.2 equivalents of the compound represented by general formula (1) as a raw material compound, in mole conversion. More specifically, in the case of potassium fluoride, it is preferably used in an amount of 1 to 1.2 equivalents, and in the case of copper iodide, it is preferably used in an amount of 0.2 to 1 equivalent.

Regarding the solvent that can be used in the production method of the present invention, it is sufficient when the solvent is inactive under the reaction condition of the reaction between the compound of general formula (1) and the compound of general formula (2), and there is not limitation on the matter. Preferred examples of the solvent to be used include aliphatic hydrocarbon-based solvents (e.g., pentane, hexane and heptane), aromatic hydrocarbons (e.g., benzene, toluene and xylene), nitriles (e.g., acetonitrile, propionitrile, phenylacetonitrile, isobutyronitrile and benzonitrile), acid amides (e.g., dimethylformamide, dimethylacetamide, methylformamide, formamide, hexamethylphosphoric triamide and N-methylpyrrolidone) and lower ethers (e.g., tetrahydrofuran, 1,2-dimethoxyethane, 1,4-dioxane, diethyl ether, 1,2-epoxyethane, 1,4-dioxane, dibutyl ether, t-butylmethyl ether and substituted tetrahydrofuran), and among them, dimethylformamide and tetrahydrofuran are more preferred. In the production method of the present invention, these solvents can be used in combination. The solvent is used in an amount of about 1 to 100 parts by weight, and preferably 1 to 10 parts by weight per 1 part by weight of the starting material. It is preferred that water is removed from the solvent to be used as much as possible, but it is not necessary to completely remove water therefrom. Water in an amount usually mixed in an industrially available solvent does not particularly become a problem at the time of carrying out the production method of the present invention, and therefore such a solvent can be directly used without removal of water.

In the production method of the present invention, it is sufficient when the raw material compound represented by general formula (1) and the raw material compound represented by general formula (2) are mixed in a solvent in the presence of the metal halide, and there is no limitation on the matter. Regarding the amount of these raw material compounds to be used, for example, the compound represented by general formula (2) is preferably used in an amount of 1 to 2 equivalents, and more preferably 1.2 to 1.5 equivalents of the compound represented by general formula (1), in mole conversion.

Further, for example, the mixing and reaction of the above-described raw material compounds is preferably performed under an inert gas atmosphere such as nitrogen and argon, the reaction temperature is preferably 40 to 80° C., the mixing time (stirring time) is preferably 5 to 20 hours, and the reaction pressure may be around ordinary pressure.

In the production method of the present invention, according to need, various methods of reaction promotion generally carried out in a Grignard reaction can be applied for the purpose of promotion of the reaction. Examples of such methods include a method in which a halogen such as bromine and iodine, an organohalide such as a Grignard reagent, ethyl bromide, methyl iodide, methylene iodide, ethyl iodide and β-bromoethyl ethyl ether, ethyl orthosilicate or the like is added to a reaction system, a method of stirring, a method of ultrasonic irradiation, etc.

As described above, the compound obtained by the production method of the present invention (produced compound), i.e., aromatic difluoroacetic acid ester is a compound represented by general formula (3):

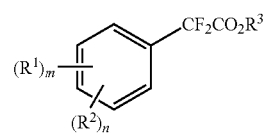

(3)

Regarding general formula (3), the explanation regarding the general formulae (1) and (2) above can be similarly applied to $R^1$, $R^2$, $R^3$, m and n.

In the production method of the present invention, methods of extraction, purification, etc. of the produced compound from the reaction system are not particularly limited, and conventionally known methods of extraction, purification, etc. can be suitably employed.

The present invention can further provide a method for producing a compound represented by general formula (4) (i.e., aromatic difluoroacetic acid) by hydrolyzing the compound represented by general formula (3).

In the compound represented by general formula (4):

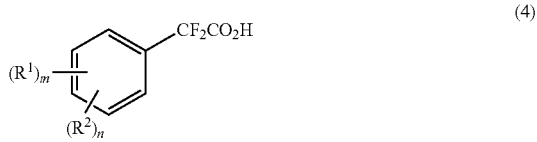

the explanation regarding the general formula (1) above can be similarly applied to $R^1$, $R^2$, m and n.

As the hydrolysis reaction of the compound represented by general formula (3), publicly-known methods, conditions, etc. of hydrolysis reaction can be suitably employed, and there is no limitation on the matter. For example, the reaction is preferably performed under an inert gas atmosphere such as nitrogen and argon, the reaction temperature is preferably 20 to 100° C., the mixing time (stirring time) is preferably 1 to 40 hours, and the reaction pressure may be around ordinary pressure. Further, methods of extraction, purification, etc. of the produced compound (the compound represented by general formula (4)) from the reaction system are not particularly limited, and conventionally known methods of extraction, purification, etc. can be suitably employed.

The compound represented by general formula (4) (i.e., aromatic difluoroacetic acid) is not limited, but for example, by decarbonating the portion of difluoroacetic acid group (—$CF_2CO_2H$) in the compound, a compound having a difluoromethyl group (—$CF_2H$) (aromatic difluoromethyl compound) can be induced. This decarbonation reaction is not limited, and for example, it is sufficient when the reaction is performed under an inert gas atmosphere such as nitrogen and argon in a solvent that is inactive under the reaction condition. Preferred examples of the solvent include those described above as the solvent that can be used in the production method of the present invention. In the decarbonation reaction, the reaction temperature is preferably 120 to 230° C., the reaction time (stirring time) is preferably 5 to 48 hours, and the reaction pressure may be around ordinary pressure. Moreover, the decarbonation reaction is preferably performed in the presence of a metal halide, in particular potassium fluoride because reaction efficiency and yield can be further increased thereby. The amount of potassium fluoride to be used is not limited, but it is preferably used in an amount of 1 to 10 equivalents, and more preferably 5 equivalents of the compound represented by general formula (4) before decarbonation, in mole conversion. Methods of extraction, purification, etc. of the produced compound (aromatic difluoromethyl compound) from the reaction system are not particularly limited, and conventionally known methods of extraction, purification, etc. can be suitably employed.

Hereinafter, the present invention will be specifically described by way of illustrative examples, but the present invention is not limited thereto.

EXAMPLES

Example 1

Production of α-Silyl Difluoroacetic Acid Ester (1)

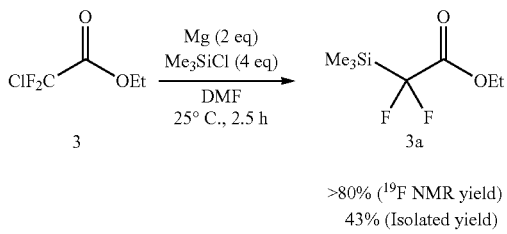

>80% ($^{19}$F NMR yield)
43% (Isolated yield)

According to the above-described scheme, magnesium (243 mg, 10.0 mmol), chlorotrimethylsilane ($Me_3SiCl$; 2.17 g, 20.0 mmol) and DMF (15 mL) were put into a two-neck reaction tube under nitrogen atmosphere. Ethyl chlorodifluoroacetate (Compound 3; 793 mg, 624 μL, 5.0 mmol) was added thereto with the reaction container being cooled in water bath, and then the mixture was stirred at room temperature for 1.5 hours. The reaction mixture was extracted with diethyl ether and washed with water, and an organic layer was dried with anhydrous sodium sulfate. Diethyl ether was distilled away under reduced pressure, and by carrying out the production by silica gel column chromatography, difluorotrimethylsilanylacetic acid ethyl ester (Compound 3a) was obtained with a yield of 43%.

Note that in other working examples, as difluorotrimethylsilanylacetic acid ethyl ester ($Me_3Si$—$CF_2CO_2Et$; Compound 3a), the product obtained in this working example was used.

The results of instrumental analysis of the product (Compound 3a) are shown below:

$^1$H-NMR ($CDCl_3$, TMS) δ4.32 (2H, q, J=7.0 Hz), 1.35 (3H, t, J=7.0 Hz), 0.237 (9H, s)

$^{19}$F-NMR ($CDCl_3$, $C_6F_6$) δ38.5 (2F, s)

Mass m/e: (m/z) (%) 181 (6), 153 (10), 125 (6), 103 (8), 77 (26), 73 (100)

Production of α-Silyl Difluoroacetic Acid Ester (2)

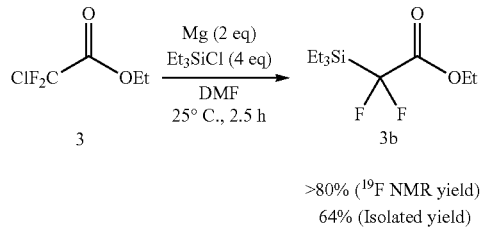

>80% ($^{19}$F NMR yield)
64% (Isolated yield)

According to the above-described scheme, magnesium (486 mg, 20.0 mmol), chlorotriethylsilane ($Et_3SiCl$; 6.03 g, 40.0 mmol) and DMF (30 mL) were put into a two-neck reaction tube under nitrogen atmosphere. Ethyl chlorodifluoroacetate (Compound 3; 1.57 g, 10.0 mmol) was added thereto with the reaction container being cooled in water bath, and then the mixture was stirred at room temperature for 1.5 hours. The reaction mixture was extracted with diethyl ether and washed with water, and an organic layer was dried with anhydrous sodium sulfate. Diethyl ether was distilled away under reduced pressure, and by carrying out the production by silica gel column chromatography, difluorotriethylsilanylacetic acid ethyl ester (Compound 3b) as α-silyl difluoroacetic acid ester was obtained with a yield of 64%.

Note that in other working examples, as difluorotriethylsilanylacetic acid ethyl ester ($Et_3Si$—$CF_2CO_2Et$; Compound 3b), the product obtained in this working example was used.

The results of instrumental analysis of the product (Compound 3b) are shown below:

$^1$H-NMR ($CDCl_3$, TMS) δ4.31 (2H, q, J=7.1 Hz), 1.35 (3H, t, J=7.1 Hz), 1.02 (9H, t, J=8.0 Hz), 0.77 (6H, q, J=8.0 Hz)

$^{19}$F-NMR ($CDCl_3$, $C_6F_6$) δ42.9 (2F, s)

Mass m/e: (m/z) (%) 209 (20), 131 (12), 115 (38), 87 (100)

Production of Aromatic Difluoroacetic Acid Ester

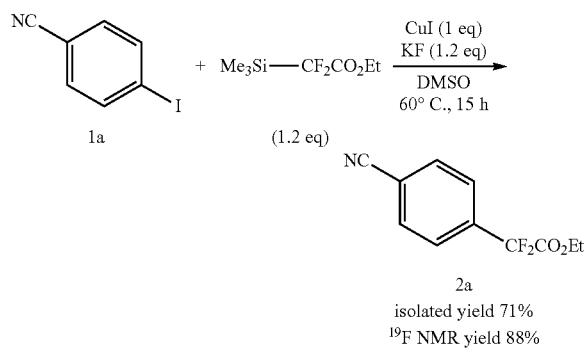

2a
isolated yield 71%
$^{19}$F NMR yield 88%

According to the above-described scheme, 4-iodobenzonitrile (Compound 1a; 68.7 mg, 0.3 mmol), difluorotrimethylsilanylacetic acid ethyl ester (Compound 3a; 70.7 mg, 0.36 mmol), copper (I) iodide (57.1 mg, 0.3 mmol), potassium fluoride (20.9 mg, 0.36 mmol) and DMSO (0.6 mL) were put into a two-neck reaction tube, and the mixture was stirred under nitrogen atmosphere at 60° C. for 15 hours. After the reaction, when trifluoroethanol (30.0 mg, 21.9 μL, 0.3 mmol) was added thereto as an internal reference to conduct $^{19}$F NMR measurement, it was found that 2-(4-cyanophenyl)-2,2-difluoroacetic acid ethyl ester (Compound 2a) as a target product was produced with a yield of 88%. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(4-cyanophenyl)-2,2-difluoroacetic acid ethyl ester (Compound 2a) was obtained with a yield of 71%.

The results of instrumental analysis of the product (Compound 2a) are shown below:

$^1$H-NMR (CDCl$_3$, TMS) δ7.78 (2H, d, J=8.8 Hz), 7.74 (2H, d, J=8.8 Hz), 4.34 (2H, q, J=7.0 Hz), 1.31 (3H, t, J=7.0 Hz)

$^{19}$F-NMR (CDCl$_3$, C$_6$F$_6$) δ56.8 (2F, s)

Mass m/e: (m/z) (%) 225 (M+, 2), 181 (2), 152 (100), 126 (4), 102 (8), 75 (4)

Production of Aromatic Difluoroacetic Acid

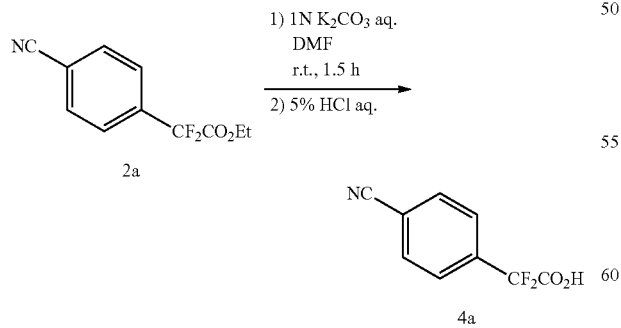

4a
isolated yield 79%

According to the above-described scheme, 2-(4-cyanophenyl)-2,2-difluoroacetic acid ethyl ester (Compound 2a; 202.7 mg, 0.9 mmol), 1N K$_2$CO$_3$ solution (2.7 mL) and DMF (2.7 mL) were put into an eggplant flask, and the mixture was stirred at 25° C. for 18 hours. After the reaction, the reaction mixture was neutralized with 5% HCl solution, extracted with ethyl acetate and washed with water, and an organic layer was dried with anhydrous sodium sulfate. Ethyl acetate was distilled away under reduced pressure, and by carrying out purification by silica gel column chromatography, 2-(4-cyanophenyl)-2,2-difluoroacetic acid (Compound 4a) was obtained with a yield of 79%.

The results of instrumental analysis of the product (Compound 4a) are shown below:

$^1$H-NMR (CDCl$_3$, TMS) δ7.80 (2H, d, J=9.2 Hz), 7.77 (2H, d, J=9.2 Hz),

$^{19}$F-NMR (CDCl$_3$, C$_6$F$_6$) δ56.3 (2F, s)

Example 2

Production of Aromatic Difluoroacetic Acid Ester

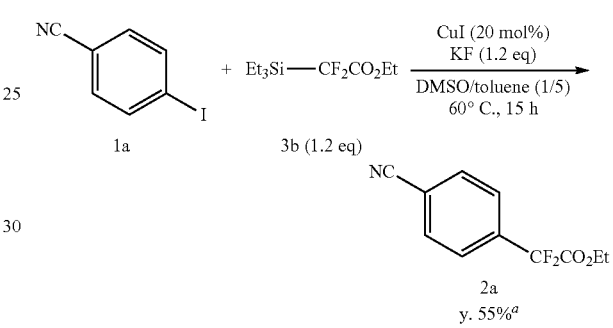

2a
y. 55%[a]

According to the above-described scheme, 4-iodobenzonitrile (Compound 1a; 68.7 mg, 0.3 mmol), copper (I) iodide (11.4 mg, 0.06 mmol), potassium fluoride (20.9 mg, 0.36 mmol), DMSO (0.1 mL) and toluene (0.5 mL) were put into a two-neck reaction tube. Then difluorotriethylsilanylacetic acid ethyl ester (Compound 3b; 85.7 mg, 85.7 μL, 0.36 mmol) was added thereto, and the mixture was stirred under nitrogen atmosphere at 60° C. for 15 hours. After the reaction, when trifluoroethanol (30.0 mg, 21.9 μL, 0.3 mmol) was added thereto as an internal reference to conduct $^{19}$F NMR measurement, it was found that 2-(4-cyanophenyl)-2,2-difluoroacetic acid ethyl ester (Compound 2a) as a target product was produced with a yield of 55%.

The results of instrumental analysis of the product (Compound 2a) are shown below:

$^{19}$F-NMR (CDCl$_3$, C$_6$F$_6$) δ56.8 (2F, s)

Mass m/e: (m/z) (%) 225 (M+, 2), 181 (2), 152 (100), 126 (4), 102 (8), 75 (4)

Example 3

Production of Aromatic Difluoroacetic Acid Ester

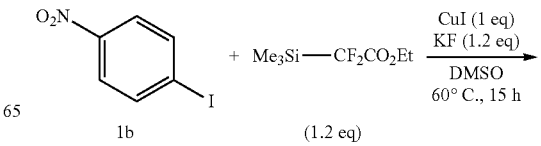

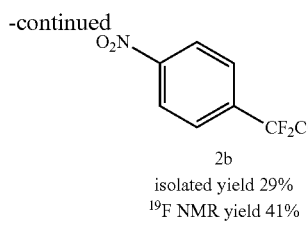

2b
isolated yield 29%
$^{19}$F NMR yield 41%

According to the above-described scheme, 4-iodonitrobenzene (Compound 1b; 74.7 mg, 0.3 mmol), difluorotrimethylsilanylacetic acid ethyl ester (Compound 3a; 70.7 mg, 0.36 mmol), copper (I) iodide (57.1 mg, 0.3 mmol), potassium fluoride (20.9 mg, 0.36 mmol) and DMSO (0.6 mL) were put into a two-neck reaction tube, and the mixture was stirred under nitrogen atmosphere at 60° C. for 15 hours. After the reaction, when trifluoroethanol (30.0 mg, 21.9 μL, 0.3 mmol) was added thereto as an internal reference to conduct $^{19}$F NMR measurement, it was found that 2,2-difluoro-2-(4-nitrophenyl)acetic acid ethyl ester (Compound 2b) as a target product was produced with a yield of 41%. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2,2-difluoro-2-(4-nitrophenyl)acetic acid ethyl ester (Compound 2b) was obtained with a yield of 29%.

The results of instrumental analysis of the product (Compound 2b) are shown below:

$^1$H-NMR (CDCl$_3$, TMS) δ8.33 (2H, d, J=9.0 Hz), 7.82 (2H, d, J=9.0 Hz), 4.33 (2H, q, J=7.0 Hz), 1.32 (1H, t, J=7.0 Hz)

$^{19}$F-NMR (CDCl$_3$, C$_6$F$_6$) δ57.2 (2F, s)

Mass m/e: (m/z) (%) 172 (100), 156 (16), 142 (16), 126 (42), 107 (5), 75 (4)

Production of Aromatic Difluoroacetic Acid

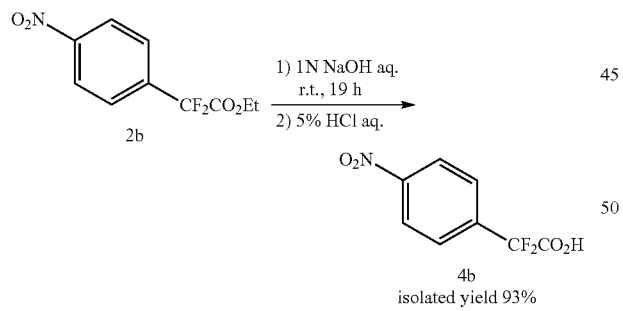

According to the above-described scheme, 2,2-difluoro-2-(4-nitrophenyl)acetic acid ethyl ester (Compound 2b; 147 mg, 0.6 mmol) and 1N NaOH solution (3 mL) were put into an eggplant flask, and the mixture was stirred at room temperature for 19 hours. After the reaction, the reaction mixture was neutralized with 5% HCl solution, extracted with ethyl acetate and washed with water, and an organic layer was dried with anhydrous sodium sulfate. Ethyl acetate was distilled away under reduced pressure, and by carrying out purification by silica gel column chromatography, 2,2-difluoro-2-(4-nitrophenyl)acetic acid (Compound 4b) was obtained with a yield of 93%.

The results of instrumental analysis of the product (Compound 4b) are shown below:

$^1$H-NMR (CDCl$_3$, TMS) δ8.34 (2H, d, J=8.8 Hz), 7.85 (2H, d, J=8.8 Hz)

$^{19}$F-NMR (CDCl$_3$, C$_6$F$_6$) δ56.7 (2F, s)

Example 4

Production of Aromatic Difluoroacetic Acid

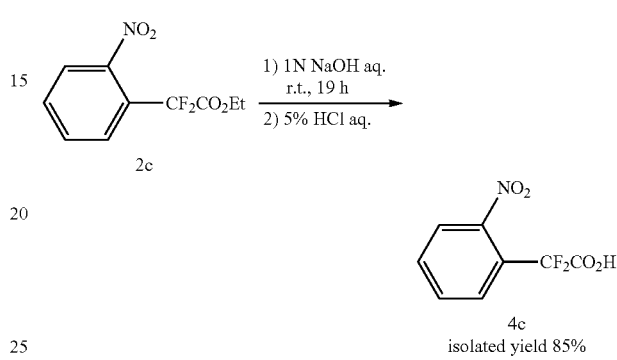

According to the above-described scheme, 2,2-difluoro-2-(2-nitrophenyl)acetic acid ethyl ester (Compound 2c; 1.01 g, 4.1 mmol) and 1N NaOH solution (10 mL) were put into an eggplant flask, and the mixture was stirred at room temperature for 19 hours. After the reaction, the reaction mixture was neutralized with 5% HCl solution, extracted with ethyl acetate and washed with water, and an organic layer was dried with anhydrous sodium sulfate. Ethyl acetate was distilled away under reduced pressure, and by carrying out purification by silica gel column chromatography, 2,2-difluoro-2-(2-nitrophenyl)acetic acid (Compound 4c) was obtained with a yield of 85%.

The results of instrumental analysis of the product (Compound 4c) are shown below:

$^1$H-NMR (CDCl$_3$, TMS) δ8.20 (1H, d, J=8.0 Hz), 7.98 (1H, d, J=8.0 Hz), 7.83 (1H, t, J=8.0 Hz), 7.75 (1H, t, J=8.0 Hz)

$^{19}$F-NMR (CDCl$_3$, C$_6$F$_6$) δ61.3 (2F, s)

Example 5

Production of Aromatic Difluoroacetic Acid Ester

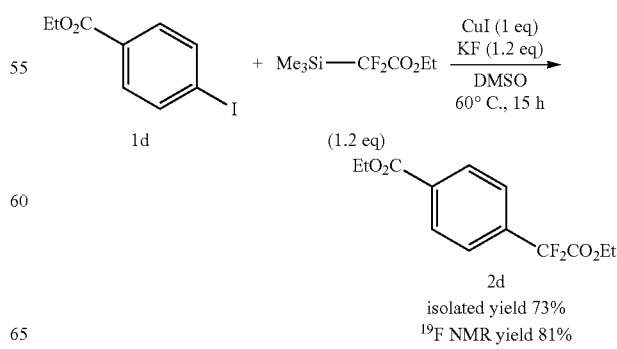

According to the above-described scheme, ethyl 4-iodobenzoate (Compound 1d; 82.8 mg, 49.9 μL, 0.3 mmol), difluorotrimethylsilanylacetic acid ethyl ester (Compound 3a; 70.7 mg, 0.36 mmol), copper (I) iodide (57.1 mg, 0.3 mmol), potassium fluoride (20.9 mg, 0.36 mmol) and DMSO (0.6 mL) were put into a two-neck reaction tube, and the mixture was stirred under nitrogen atmosphere at 60° C. for 15 hours. After the reaction, when trifluoroethanol (30.0 mg, 21.9 μL, 0.3 mmol) was added thereto as an internal reference to conduct $^{19}$F NMR measurement, it was found that 4-(2-ethoxy-1,1-difluoro-2-oxoethyl)benzoic acid ethyl ester (Compound 2d) as a target product was produced with a yield of 81%. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 4-(2-ethoxy-1,1-difluoro-2-oxoethyl)benzoic acid ethyl ester (Compound 2d) was obtained with a yield of 73%.

The results of instrumental analysis of the product (Compound 2d) are shown below:

$^1$H-NMR (CDCl$_3$, TMS) δ8.13 (2H, d, J=8.2 Hz), 7.68 (2H, d, J=8.2 Hz), 4.41 (2H, q, J=7.2 Hz), 4.30 (2H, q, J=7.2 Hz), 1.41 (3H, J=7.2 Hz), 1.30 (3H, J=7.2 Hz)

$^{19}$F-NMR (CDCl$_3$, C$_6$F$_6$) δ57.2 (2F, s) Mass m/e: (m/z) (%) 272 (M+, 2), 227 (15), 199 (100), 171 (34), 126 (14)

Production of Aromatic Difluoroacetic Acid

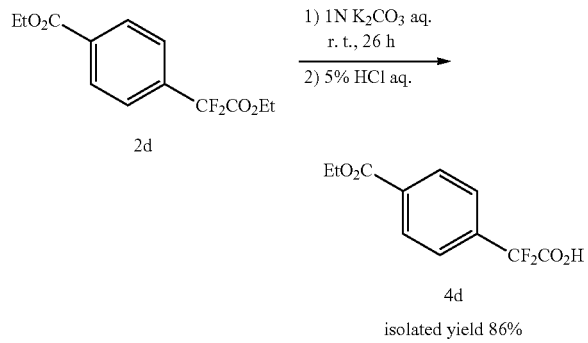

According to the above-described scheme, 4-(2-ethoxy-1,1-difluoro-2-oxoethyl)benzoic acid ethyl ester (Compound 2d; 108.9 mg, 0.4 mmol) and 1N K$_2$CO$_3$ solution (1.5 mL) were put into an eggplant flask, and the mixture was stirred at room temperature for 26 hours. After the reaction, the reaction mixture was neutralized with 5% HCl solution, extracted with ethyl acetate and washed with water, and an organic layer was dried with anhydrous sodium sulfate. Ethyl acetate was distilled away under reduced pressure, and by carrying out purification by silica gel column chromatography, 4-(2-ethoxy-1,1-difluoro-2-oxoethyl)benzoic acid (Compound 4d) was obtained with a yield of 86%.

The results of instrumental analysis of the product (Compound 4d) are shown below:

$^1$H-NMR (CDCl$_3$, TMS) δ8.13 (2H, d, J=8.0 Hz), 7.71 (2H, d, J=8.0 Hz), 4.41 (2H, q, J=7.2 Hz), 1.40 (3H, t, J=7.2 Hz)

$^{19}$F-NMR (CDCl$_3$, C$_6$F$_6$) δ56.6 (2F, s)

Example 6

Production of Aromatic Difluoroacetic Acid

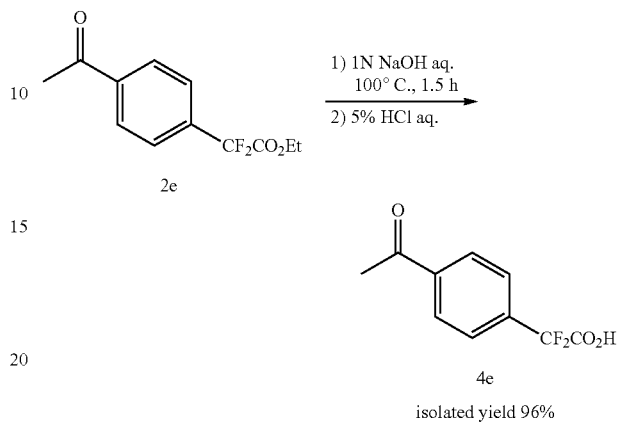

According to the above-described scheme, 2-(4-acetylphenyl)-2,2-difluoroacetic acid ethyl ester (Compound 2e; 436.0 mg, 1.8 mmol) and 1N NaOH solution (3.0 mL) were put into an eggplant flask, and the mixture was stirred at 100° C. for 1.5 hours. After the reaction, the reaction mixture was neutralized with 5% HCl solution, extracted with ethyl acetate and washed with water, and an organic layer was dried with anhydrous sodium sulfate. Ethyl acetate was distilled away under reduced pressure, and by carrying out purification by silica gel column chromatography, 2-(4-acetylphenyl)-2,2-difluoroacetic acid (Compound 4e) was obtained with a yield of 96%.

The results of instrumental analysis of the product (Compound 4e) are shown below:

$^1$H-NMR (CDCl$_3$, TMS) δ8.05 (2H, d, J=8.4 Hz), 7.75 (2H, d, J=8.4 Hz), 2.65 (3H, s)

$^{19}$F-NMR (CDCl$_3$, C$_6$F$_6$) δ56.6 (2F, s)

Example 7

Production of Aromatic Difluoroacetic Acid Ester

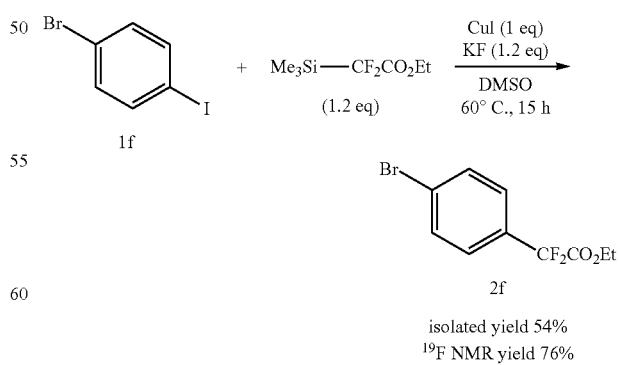

According to the above-described scheme, 4-bromoiodobenzene (Compound 1f; 84.9 mg, 0.3 mmol), difluorotrimethylsilanylacetic acid ethyl ester (Compound 3a; 70.7 mg, 0.36 mmol), copper (I) iodide (57.1 mg, 0.3 mmol), potassium fluoride (20.9 mg, 0.36 mmol) and DMSO (0.6 mL) were put into a two-neck reaction tube, and the mixture was stirred under nitrogen atmosphere at 60° C. for 15 hours. After the reaction, when trifluoroethanol (30.0 mg, 21.9 µL, 0.3 mmol) was added thereto as an internal reference to conduct $^{19}$F NMR measurement, it was found that 2-(4-bromophenyl)-2,2-difluoroacetic acid ethyl ester (Compound 2f) as a target product was produced with a yield of 76%. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(4-bromophenyl)-2,2-difluoroacetic acid ethyl ester (Compound 2f) was obtained with a yield of 54%.

The results of instrumental analysis of the product (Compound 2f) are shown below:

$^{1}$H-NMR (CDCl$_{3}$, TMS) δ7.60 (2H, d, J=8.6 Hz), 7.48 (2H, d, J=8.6 Hz), 4.30 (2H, q, J=7.2 Hz), 1.31 (3H, t, J=7.2 Hz)

$^{19}$F-NMR (CDCl$_{3}$, C$_{6}$F$_{6}$) δ57.6 (2F, s) Mass m/e: (m/z) (%) 280 (M+2, 12), 278 (M+, 12), 207 (94), 205 (100), 126 (32), 75 (8)

Production of Aromatic Difluoroacetic Acid

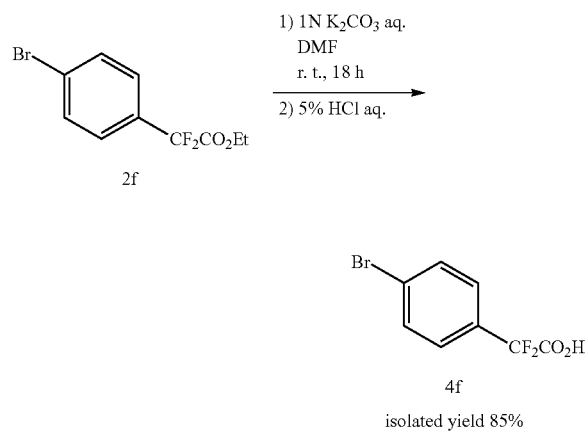

According to the above-described scheme, 2-(4-bromophenyl)-2,2-difluoroacetic acid ethyl ester (Compound 2f; 279.1 mg, 1.0 mmol), 1N K$_{2}$CO$_{3}$ solution (3.0 mL) and DMF (3.0 mL) were put into an eggplant flask, and the mixture was stirred at 25° C. for 18 hours. After the reaction, the reaction mixture was neutralized with 5% HCl solution, extracted with ethyl acetate and washed with water, and an organic layer was dried with anhydrous sodium sulfate. Ethyl acetate was distilled away under reduced pressure, and by carrying out purification by silica gel column chromatography, 2-(4-bromophenyl)-2,2-difluoroacetic acid (Compound 4f) was obtained with a yield of 85%.

The results of instrumental analysis of the product (Compound 4f) are shown below:

$^{1}$H-NMR (CDCl$_{3}$, TMS) δ7.61 (2H, d, J=8.8 Hz), 7.50 (2H, d, J=8.8 Hz)

$^{19}$F-NMR (CDCl$_{3}$, C$_{6}$F$_{6}$) δ56.7 (2F, s)

Example 8

Production of Aromatic Difluoroacetic Acid Ester

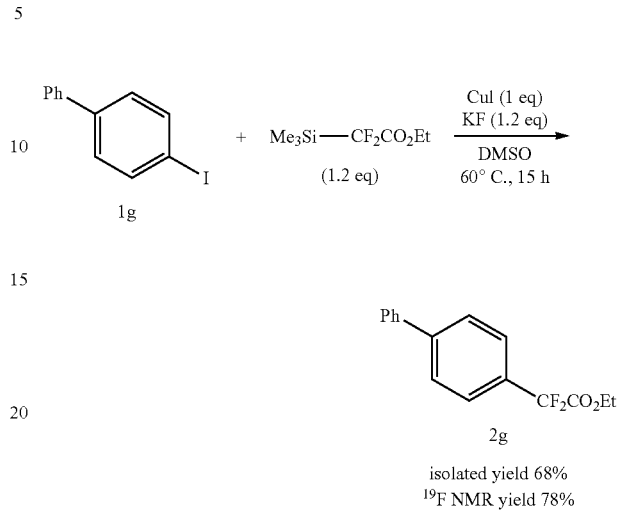

According to the above-described scheme, 4-iodobiphenyl (Compound 1g; 84.0 mg, 0.3 mmol), difluorotrimethylsilanylacetic acid ethyl ester (Compound 3a; 70.7 mg, 0.36 mmol), copper (I) iodide (57.1 mg, 0.3 mmol), potassium fluoride (20.9 mg, 0.36 mmol) and DMSO (0.6 mL) were put into a two-neck reaction tube, and the mixture was stirred under nitrogen atmosphere at 60° C. for 15 hours. After the reaction, when trifluoroethanol (30.0 mg, 21.9 µL, 0.3 mmol) was added thereto as an internal reference to conduct $^{19}$F NMR measurement, it was found that 2-(biphenyl-4-yl)-2,2-difluoroacetic acid ethyl ester (Compound 2g) as a target product was produced with a yield of 78%. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(biphenyl-4-yl)-2,2-difluoroacetic acid ethyl ester (Compound 2g) was obtained with a yield of 68%.

The results of instrumental analysis of the product (Compound 2g) are shown below:

$^{1}$H-NMR (CDCl$_{3}$, TMS) δ7.38-7.70 (9H, m), 4.35 (2H, q, J=7.2 Hz), 1.33 (3H, t, J=7.2 Hz)

$^{19}$F-NMR (CDCl$_{3}$, C$_{6}$F$_{6}$) δ58.3 (2F, s)

Mass m/e: (m/z) (%) 276 (M+, 21), 203 (100), 183 (6), 152 (6)

Production of Aromatic Difluoroacetic Acid

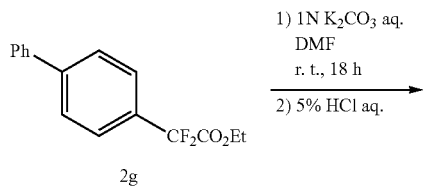

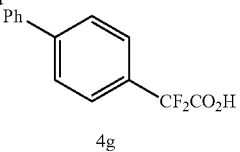

4g isolated yield 88%

According to the above-described scheme, 2-(biphenyl-4-yl)-2,2-difluoroacetic acid ethyl ester (Compound 2g; 82.9 mg, 0.3 mmol), 1N $K_2CO_3$ solution (0.9 mL) and DMF (0.9 mL) were put into an eggplant flask, and the mixture was stirred at room temperature for 18 hours. After the reaction, the reaction mixture was neutralized with 5% HCl solution, extracted with ethyl acetate and washed with water, and an organic layer was dried with anhydrous sodium sulfate. Ethyl acetate was distilled away under reduced pressure, and by carrying out purification by silica gel column chromatography, 2-(biphenyl-4-yl)-2,2-difluoroacetic acid (Compound 4g) was obtained with a yield of 88%.

The results of instrumental analysis of the product (Compound 4g) are shown below:

$^1$H-NMR (CDCl$_3$, TMS) δ7.37-7.714 (9H, m)
$^{19}$F-NMR (CDCl$_3$, C$_6$F$_6$) δ56.9 (2F, s)

Comparative Example 1

Production of Aromatic Difluoroacetic Acid Ester

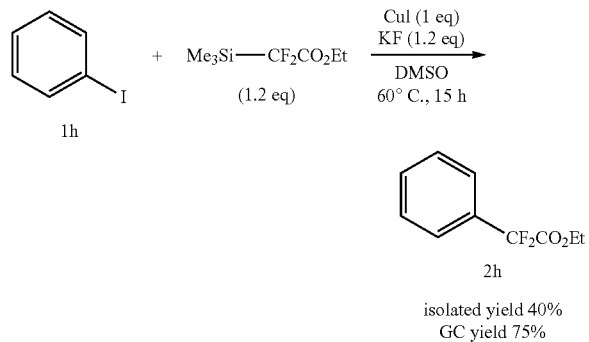

2h isolated yield 40%
GC yield 75%

According to the above-described scheme, 4-iodobenzene (Compound 1h; 61.2 mg, 33.4 μL, 0.3 mmol), difluorotrimethylsilanylacetic acid ethyl ester (Compound 3a; 70.7 mg, 0.36 mmol), copper (I) iodide (57.1 mg, 0.3 mmol), potassium fluoride (20.9 mg, 0.36 mmol) and DMSO (0.6 mL) were put into a two-neck reaction tube, and the mixture was stirred under nitrogen atmosphere at 60° C. for 15 hours. After the reaction, when the mixture was analyzed by GC-Mass, it was found that 2-(phenyl)-2,2-difluoroacetic acid ethyl ester (Compound 2h) as a target product was produced with a conversion rate of 76%. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(phenyl)-2,2-difluoroacetic acid ethyl ester (Compound 2h) was obtained with a yield of 40%.

The results of instrumental analysis of the product (Compound 2h) are shown below:

$^1$H-NMR (CDCl$_3$, TMS) δ7.61 (2H, d, J=9.2 Hz) 7.44-7.52 (3H, m), 4.30 (2H, q, J=7.2 Hz), 1.31 (3H, t, J=7.2 Hz)
$^{19}$F-NMR (CDCl$_3$, C$_6$F$_6$) δ57.8 (2F, s)
Mass m/e: (m/z) (%) 200 (M+, 8), 127 (100), 77 (6)

Comparative Example 2

Production of Aromatic Difluoroacetic Acid Ester

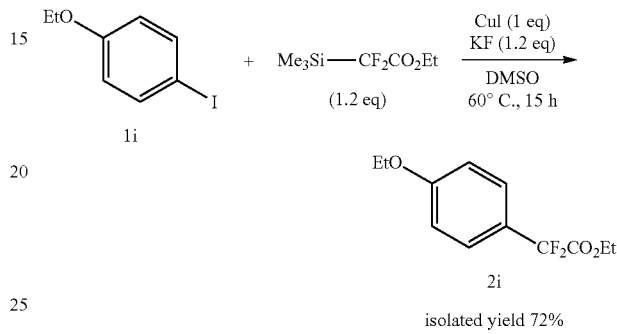

2i isolated yield 72%

According to the above-described scheme, 4-iodophenetole (Compound 1i; 74.7 mg, 0.3 mmol), difluorotrimethylsilanylacetic acid ethyl ester (Compound 3a; 70.7 mg, 0.36 mmol), copper (I) iodide (57.1 mg, 0.3 mmol), potassium fluoride (20.9 mg, 0.36 mmol) and DMSO (0.6 mL) were put into a two-neck reaction tube, and the mixture was stirred under nitrogen atmosphere at 60° C. for 15 hours. After the reaction, when trifluoroethanol (30.0 mg, 21.9 μL, 0.3 mmol) was added thereto as an internal reference to conduct $^{19}$F NMR measurement, it was found that 2-(4-ethoxyphenyl)-2,2-difluoroacetic acid ethyl ester (Compound 2i) as a target product was produced with a yield of 78%. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(4-ethoxyphenyl)-2,2-difluoroacetic acid ethyl ester (Compound 2i) was obtained with a yield of 72%.

The results of instrumental analysis of the product (Compound 2i) are shown below:

$^1$H-NMR (CDCl$_3$, TMS) δ7.52 (2H, d, J=8.8 Hz), 6.93 (2H, d, J=8.8 Hz), 4.29 (2H, q, J=7.2 Hz), 4.06 (2H, q, J=7.0 Hz), 1.43 (3H, t, J=7.0 Hz), 1.30 (3H, t, J=7.2 Hz)
$^{19}$F-NMR (CDCl$_3$, C$_6$F$_6$) δ59.2 (2F, s)
Mass m/e: (m/z) (%) 244 (M+, 12), 171 (98), 143 (100), 126 (4)

Comparative Example 3

Production of Aromatic Difluoroacetic Acid Ester

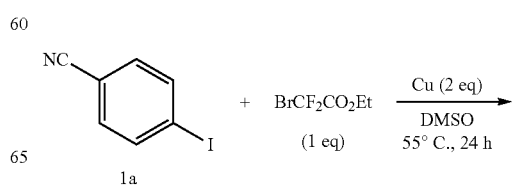

1a

-continued

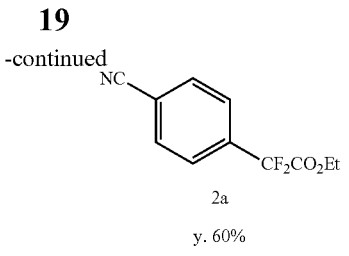

y. 60%

According to the Kumadaki method (K. Sato et al., Chem. Pharm. Bull., vol. 47 p. 1013 (1999)) and the above-described scheme, 4-iodobenzonitrile (Compound 1a; 343.5 mg, 1.5 mmol), bromodifluoroacetic acid ethyl ester (304.5 mg, 1.5 mmol), copper powder (190.5 mg, 3.0 mmol) and DMSO (3.0 mL) were put into a two-neck reaction tube, and the mixture was stirred under argon atmosphere at 55° C. for 24 hours. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(4-cyanophenyl)-2,2-difluoroacetic acid ethyl ester (Compound 2a) was obtained with a yield of 60%.

The results of instrumental analysis of the product (Compound 2a) are shown below:

$^1$H-NMR (CDCl$_3$, TMS) δ7.78 (2H, d, J=8.8 Hz), 7.74 (2H, d, J=8.8 Hz), 4.34 (2H, q, J=7.0 Hz), 1.31 (3H, t, J=7.0 Hz)

$^{19}$F-NMR (CDCl$_3$, C$_6$F$_6$) δ56.8 (2F, s)

Mass m/e: (m/z) (%) 225 (M+, 2), 181 (2), 152 (100), 126 (4), 102 (8), 75 (4)

Comparative Example 4

Production of Aromatic Difluoroacetic Acid Ester

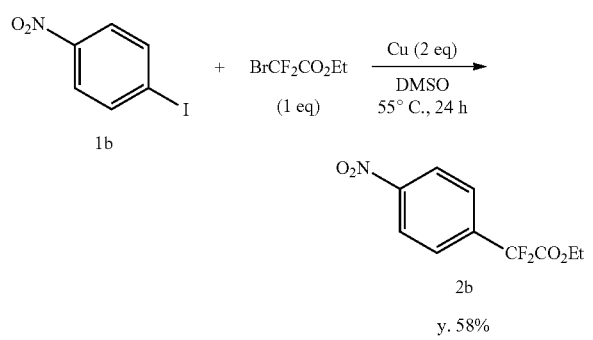

According to the Kumadaki method (supra) and the above-described scheme, 4-iodonitrobenzene (Compound 1b; 249.0 mg, 1.0 mmol), bromodifluoroacetic acid ethyl ester (203 mg, 1.0 mmol), copper powder (128 mg, 2.0 mmol) and DMSO (2.0 mL) were put into a two-neck reaction tube, and the mixture was stirred under argon atmosphere at 55° C. for 15 hours. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2,2-difluoro-2-(4-nitrophenyl)acetic acid ethyl ester (Compound 2b) was obtained with a yield of 58%.

The results of instrumental analysis of the product (Compound 2b) are shown below:

$^1$H-NMR (CDCl$_3$, TMS) δ8.33 (2H, d, J=9.0 Hz), 7.82 (2H, d, J=9.0 Hz), 4.33 (2H, q, J=7.0 Hz), 1.32 (1H, t, J=7.0 Hz)

$^{19}$F-NMR (CDCl$_3$, C$_6$F$_6$) δ57.2 (2F, s)

Mass m/e: (m/z) (%) 172 (100), 156 (16), 142 (16), 126 (42), 107 (5), 75 (4)

Comparative Example 5

Production of Aromatic Difluoroacetic Acid Ester

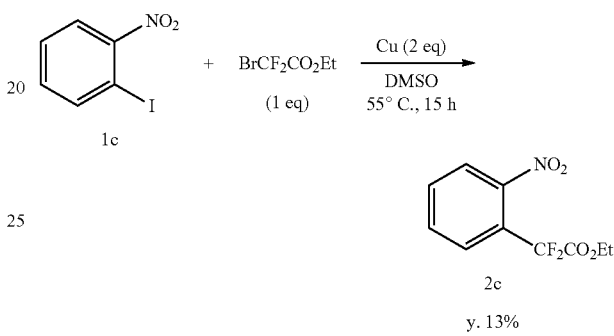

y. 13%

According to the Kumadaki method (supra) and the above-described scheme, 2-iodonitrobenzene (Compound 1c; 250.0 mg, 1.0 mmol), bromodifluoroacetic acid ethyl ester (203 mg, 1.0 mmol), copper powder (128 mg, 2.0 mmol) and DMSO (2.0 mL) were put into a two-neck reaction tube, and the mixture was stirred under argon atmosphere at 55° C. for 15 hours. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2,2-difluoro-2-(2-nitrophenyl)acetic acid ethyl ester (Compound 2c) was obtained with a yield of 13%.

The results of instrumental analysis of the product (Compound 2c) are shown below:

$^1$H-NMR (CDCl$_3$, TMS) δ8.15 (1H, d, J=7.8 Hz), 7.96 (1H, d, J=7.8 Hz), 7.80 (1H, t, J=7.8 Hz), 7.72 (1H, t, J=7.8 Hz), 4.39 (2H, q, J=7.2 Hz), 1.35 (3H, t, J=7.2 Hz)

$^{19}$F-NMR (CDCl$_3$, C$_6$F$_6$) δ61.8 (2F, s) Mass m/e: (m/z) (%) 200 (4), 199 (5), 172 (100), 156 (68), 143 (96), 126 (62), 95 (79)

Comparative Example 6

Production of Aromatic Difluoroacetic Acid Ester

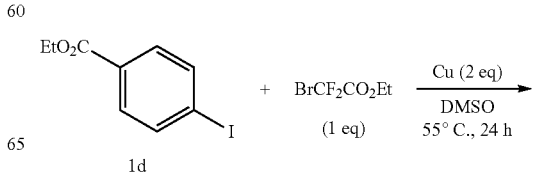

-continued

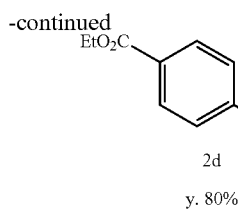

y. 80%

According to the Kumadaki method (supra) and the above-described scheme, ethyl 4-iodobenzoate (Compound 1d; 1.38 g, 5.0 mmol), bromodifluoroacetic acid ethyl ester (1.015 g, 5.0 mmol), copper powder (635.5 mg, 10.0 mmol) and DMSO (10 mL) were put into a two-neck reaction tube, and the mixture was stirred under argon atmosphere at 55° C. for 24 hours. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 4-(2-ethoxy-1,1-difluoro-2-oxethyl)benzoic acid ethyl ester (Compound 2d) was obtained with a yield of 80%.

The results of instrumental analysis of the product (Compound 2d) are shown below:

$^1$H-NMR (CDCl$_3$, TMS) δ8.13 (2H, d, J=8.2 Hz), 7.68 (2H, d, J=8.2 Hz), 4.41 (2H, q, J=7.2 Hz), 4.30 (2H, q, J=7.2 Hz), 1.41 (3H, t, J=7.2 Hz), 1.30 (3H, J=7.2 Hz)

$^{19}$F-NMR (CDCl$_3$, C$_6$F$_6$) δ57.2 (2F, s)

Mass m/e: (m/z) (%) 272 (M+, 2), 227 (15), 199 (100), 171 (34), 126 (14)

Comparative Example 7

Production of Aromatic Difluoro Acetic Acid Ester

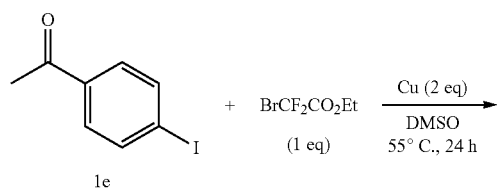

y. 82%

According to the Kumadaki method (supra) and the above-described scheme, 4-iodoacetophenone (Compound 1e; 1.23 g, 5.0 mmol), bromodifluoroacetic acid ethyl ester (1.22 g, 6.0 mmol), copper powder (768.0 mg, 12.0 mmol) and DMSO (10.0 mL) were put into a two-neck reaction tube, and the mixture was stirred under argon atmosphere at 55° C. for 24 hours. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(4-acetylphenyl)-2,2-difluoroacetic acid ethyl ester (Compound 2e) was obtained with a yield of 82%.

The results of instrumental analysis of the product (Compound 2e) are shown below:

$^1$H-NMR (CDCl$_3$, TMS) δ8.04 (2H, d, J=8.4 Hz), 7.72 (2H, d, J=8.4 Hz), 4.31 (2H, q, J=7.2 Hz), 2.64 (3H, s), 1.31 (3H, t, J=7.2 Hz)

$^{19}$F-NMR (CDCl$_3$, C$_6$F$_6$) δ57.2 (2F, s)

Mass m/e: (m/z) (%) 242 (M+, 13), 227 (59), 199 (20), 169 (100), 154 (13), 126 (34)

Comparative Example 8

Production of Aromatic Difluoroacetic Acid Ester

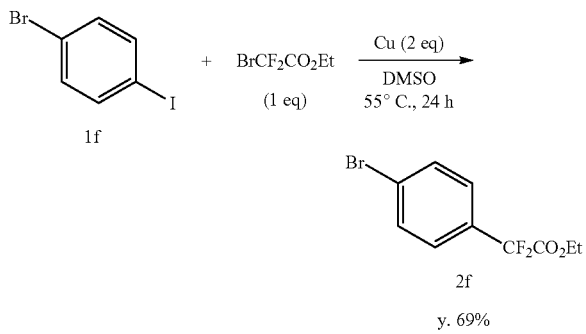

y. 69%

According to the Kumadaki method (supra) and the above-described scheme, 4-bromoiodobenzene (848.7 mg, 3.0 mmol), bromodifluoroacetic acid ethyl ester (Compound 1f; 608.9 mg, 3.0 mmol), copper powder (381 mg, 6.0 mmol) and DMSO (6.0 mL) were put into a two-neck reaction tube, and the mixture was stirred under argon atmosphere at 55° C. for 24 hours. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(4-bromophenyl)-2,2-difluoroacetic acid ethyl ester (Compound 2f) was obtained with a yield of 69%.

The results of instrumental analysis of the product (Compound 2f) are shown below:

$^1$H-NMR (CDCl$_3$, TMS) δ7.60 (2H, d, J=8.6 Hz), 7.48 (2H, d, J=8.6 Hz), 4.30 (2H, q, J=7.2 Hz), 1.31 (3H, t, J=7.2 Hz)

$^{19}$F-NMR (CDCl$_3$, C$_6$F$_6$) δ57.6 (2F, s)

Mass m/e: (m/z) (%) 280 (M+2, 12), 278 (M, 12), 207 (94), 205 (100), 126 (32), 75 (8)

Comparative Example 9

Production of Aromatic Difluoroacetic Acid Ester

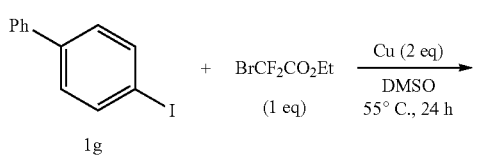

-continued

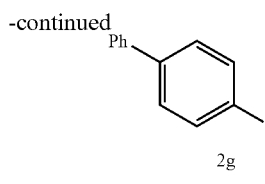

2g
y. 65%

According to the Kumadaki method (supra) and the above-described scheme, 4-iodobiphenyl (Compound 1g; 840.3 mg, 3.0 mmol), bromodifluoroacetic acid ethyl ester (609.0 mg, 3.0 mmol), copper powder (381.0 mg, 6.0 mmol) and DMSO (6.0 mL) were put into a two-neck reaction tube, and the mixture was stirred under argon atmosphere at 55° C. for 24 hours. The reaction mixture was extracted with ethyl acetate and washed with water, and an organic layer was dried with anhydrous sodium sulfate. Ethyl acetate was distilled away under reduced pressure, and by carrying out purification by silica gel column chromatography, 2-(biphenyl-4-yl)-2,2-difluoroacetic acid ethyl ester (Compound 2g) was obtained with a yield of 65%.

The results of instrumental analysis of the product (Compound 2g) are shown below:

$^1$H-NMR (CDCl$_3$, TMS) δ7.38-7.70 (9H, m), 4.35 (2H, q, J=7.2 Hz), 1.33 (3H, t, J=7.2 Hz)

$^{19}$F-NMR (CDCl$_3$, C$_6$F$_6$) δ58.3 (2F, s)

Mass m/e: (m/z) (%) 276 (M+, 21), 203 (100), 183 (6), 152 (6)

INDUSTRIAL APPLICABILITY

According to the present invention, it is possible to provide a method for producing a compound having a difluoromethylene group at an even lower cost and with excellent yield. The method of the present invention is highly useful because, for example, it is possible to produce an aromatic difluoroacetic acid ester or aromatic difluoroacetic acid at a low cost and with a high yield.

The invention claimed is:

1. A method for producing a compound represented by the following general formula (4):

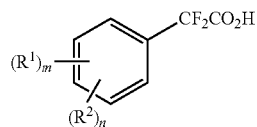

(4)

wherein in the general formula (4), $R^1$ each independently represents an electroattracting group, $R^2$ each independently represents a monovalent organic group, m is an integer from 1 to 3 and n is an integer from 0 to (5-m), the compound being obtained by reacting a compound represented by the following general formula (1):

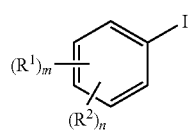

(1)

wherein in the general formula (1), $R^1$ each independently represents an electroattracting group, $R^2$ each independently represents a monovalent organic group, m is an integer from 1 to 3 and n is an integer from 0 to (5-m), and a compound represented by the following general formula (2):

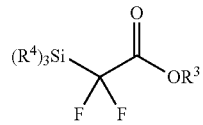

(2)

wherein in the general formula (2), $R^3$ represents a monovalent organic group and $R^4$ each independently represents at least one selected from the group consisting of a substituted or unsubstituted methyl group, ethyl group, propyl group, isopropyl group and phenyl group, in the presence of a metal halide, to obtain a compound of general formula (3):

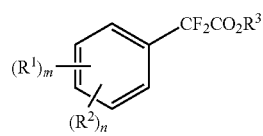

(3)

wherein in the general formula (3), $R^1$ each independently represents an electroattracting group, $R^2$ each independently represents a monovalent organic group, $R^3$ represents a monovalent organic group, m is an integer from 1 to 3 and n is an integer from 0 to (5-m), and hydrolyzing the compound of formula (3).

2. The method according to claim 1, wherein the metal halide is potassium fluoride or copper iodide.

3. The method according to claim 1, wherein the $R^1$ is a linking group in the ortho position and/or the meta position.

4. The method according to claim 1, wherein the $R^1$ is at least one selected from the group consisting of a cyano group, a nitro group, a substituted or unsubstituted alkylacetic acid ester group, a substituted or unsubstituted alkylcarbonyl group, a halogen group and a substituted or unsubstituted phenyl group.

5. The method according to claim 1, wherein the $R^2$ is at least one selected from the group consisting of an alkyl group, a cycloalkyl group, an aryl group, an alkenyl group and an alkynyl group.

6. The method according to claim 1, wherein the $R^3$ is at least one selected from the group consisting of an alkyl group, a cycloalkyl group, an aryl group, an alkenyl group and an alkynyl group.

7. The method according to claim 1 or 2, wherein the compound represented by the general formula (2) is obtained by reacting a compound represented by the following general formula (5):

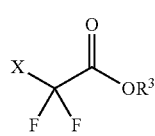

(5)

wherein in the general formula (5), $R^3$ represents a monovalent organic group and X represents a halogen group, and a compound represented by the following general formula (6):

$$(R^4)_3SiX \qquad (6)$$

wherein in the general formula (6), $R^4$ each independently represents at least one selected from the group consisting of a substituted or unsubstituted methyl group, ethyl group, propyl group, isopropyl group and phenyl group, and X represents a halogen group.

8. The method according to claim 7, wherein the X is a chlorine atom.

9. The method according to claim 7, wherein a reaction of the compound represented by the general formula (5) and the compound represented by the general formula (6) is performed in the presence of magnesium.

* * * * *